(12) United States Patent
Bango (10) Patent No.: US 11,300,484 B1
(45) Date of Patent: Apr. 12, 2022

(54) METHOD FOR ANALYSIS OF AEROSOLIZED BIOLOGICAL SPECIES IN EPIDEMIC AND PANDEMIC PREDICTION

(71) Applicant: Joseph J. Bango, New Haven, CT (US)

(72) Inventor: Joseph J. Bango, New Haven, CT (US)

(73) Assignee: Connecticut Analytical Corporation, Bethany, CT (US)

( * ) Notice: Subject to any disclaimer, the term of this patent is extended or adjusted under 35 U.S.C. 154(b) by 82 days.

(21) Appl. No.: 15/732,259

(22) Filed: Oct. 16, 2017

(51) Int. Cl.
| | |
|---|---|
| *G01N 1/22* | (2006.01) |
| *G01N 1/26* | (2006.01) |
| *G01N 1/24* | (2006.01) |
| *G01N 1/02* | (2006.01) |

(52) U.S. Cl.
CPC ......... *G01N 1/2273* (2013.01); *G01N 1/2208* (2013.01); *G01N 1/24* (2013.01); *G01N 1/26* (2013.01); *G01N 2001/021* (2013.01); *G01N 2001/2223* (2013.01)

(58) Field of Classification Search
CPC .... C12Q 1/6869; C12Q 1/6872; G01N 15/12; G01N 1/2273; G01N 1/2208; G01N 1/26; G01N 1/24; G01N 2001/021; G01N 2001/2223
USPC ............... 250/339.06, 339.08; 356/326–330; 73/863.02, 28.05, 28.06, 31.01, 31.02, 73/863.22, 863.31, 863.33, 864.73, 73/864.81
See application file for complete search history.

(56) References Cited

U.S. PATENT DOCUMENTS

| | | | | |
|---|---|---|---|---|
| 2005/0266415 A1* | 12/2005 | Ryan | ......................... | C12Q 1/04 435/6.19 |
| 2008/0190219 A1* | 8/2008 | Jensen | ...................... | C12Q 1/24 73/864.71 |
| 2011/0029253 A1* | 2/2011 | Miller | ....................... | G01N 1/26 702/22 |
| 2011/0252897 A1* | 10/2011 | Swenson | .............. | G01N 1/2208 73/863 |
| 2012/0174650 A1* | 7/2012 | Ariessohn | ............... | B08B 7/026 73/23.2 |
| 2016/0069919 A1* | 3/2016 | Holmes | .............. | G01N 35/0092 506/2 |
| 2019/0250785 A1* | 8/2019 | Pandolfi | ............... | G01C 21/206 |

* cited by examiner

*Primary Examiner* — Robert R Raevis
(74) *Attorney, Agent, or Firm* — Michael A. Blake (57) ABSTRACT

The disclosed invention is a new concept for a network of specialized continuous ambient air sampling systems, which employ a novel non-destructive ionization and separation method, coupled to a near real-time genomic sequencer. The network of preferably pathogen samplers, would constitute a plurality of distributed nodes throughout the world, with bacterial & viral concentration, identification, and mutation data uploaded to the cloud for epidemic/pandemic predictive modeling. The proposed system offers the ability to migrate from outbreak surveillance, to outbreak forecast. In addition, the capability for continuous data of genomic sequencing offers an enhanced capability to help track antigenic drift and antigenic shift. While optimized for viral capture and analysis, any airborne pathogen or spore can be accepted using the technology. Applications include world health monitoring, pandemic prediction, and detection of real-time bioterror pathogen deployment.

14 Claims, 7 Drawing Sheets

Electrospray Ionization Process of Bio-Aerosol Species, with nanopore analysis

Figure 1

Electrospray Ionization Process of Bio-Aerosol Species, with nanopore analysis

40 — Electrospray (ES) Source with Aerosols Captured from Air and Charged with ES 80 — Ambient Bio-Aerosols 120 — Capillary Tube

130 — Skimmers

140 — Image Charge Detector Tube

150 — Discharge Target

160 — PicoAmmeter & PC

210 Cathode Ray Tube

220 Charged Particle Detection Delivery System

METHOD FOR ANALYSIS OF AEROSOLIZED BIOLOGICAL SPECIES IN EPIDEMIC AND PANDEMIC PREDICTION

BACKGROUND

Field of Invention

The present invention relates generally to the field of mass spectrometry and in particular to Charge Detection Mass Spectrometry. In addition, the present invention relates to genetic sequencing.

Description of Related Art

As far back as the $14^{th}$ century, there have been attempts to predict the evolution and spread of disease. There was no prediction for the The Black Death of 1347-1353, and no historical evidence of any knowledge regarding a vaccine. It has been documented that the inoculation of dried pox-pus was practiced in Persia and India as an operation where the surface of the body was injured with needles or lancets, and foreign puss from "pox" or perhaps other disease effusions were placed into direct contact with the bloody wound or bloodstream of the inoculation recipient. Among the Arabs, there are accounts that citizens would "purchase the pox," by exchanging raisins and other fruits with an infected person who would serve as the donor of the lymph (Pylarini, Phil Trans., 1716 Vol XXIV., p, 393)

Until recently, most epidemic prediction relied on models based on the weather, tying climate parameters "and the occurrence of infectious diseases and/or their vectors in order to predict geographical and temporal patterns of disease." Of recent date however, new computer models have yielded a new and powerful tool in the prediction of disease and disease transmission. Disease surveillance, principally from hospitals and clinics, and to a lesser extent social media, is the principal source for the software-input variables. The prediction of emerging biological threats has been assigned the level of national security beginning with the administration of President Bill Clinton. An expert in the field was, for the first time in U.S. history, appointed to the National Security Council.

When faced with analyzing large populations, deterministic or compartmental mathematical models are employed for epidemic probability modeling. In the deterministic model, individuals in the population are assigned to different subgroups or compartments, each representing a specific stage of the epidemic. The transition rates from one class to another are mathematically expressed as derivatives; hence the model is formulated using differential equations. While building such models, it must be assumed that the population size in a compartment is differentiable with respect to time and that the epidemic process is deterministic. In other words, the changes in population of a compartment can be calculated using only the history used to develop the model (Brauer & Castillo-Chavez, 2001).

Regardless of the method of modeling, the input variables are always the result of data obtained from hospitals or clinics with confirmed cases of the communicable disease under investigation. In some cases, weather, air travel, and social media data can provide additional factors that can improve predicative model accuracy. However, this may not always be the case if the additional information is not suitably filtered. As a result, additional data can add 'noise' to the system, reducing the model accuracy. An example of what a simple system based entirely on information obtained from the Pan American Health Organization (PAHO). "PAHO data are easy to handle and manage which is an important advantage. Additionally, they are publicly available and there is a constant flow of new data every week which results in constant update of the predictive models". A recent successful DARPA predictive modeling challenge for Chikungunya fever "applied models that were very simple with 2-3 parameters to tune. Models with more parameters needed more and more diverse data in order to be predictive. The total patience-counting time-series followed a sigmoid function as in typical SIR models. The hardest problem in the challenge was to forecast the time-series from the onset of the outbreak. Early-stage predictions seem very hard because the factors that affect the dynamics were more or less unknown. Safer predictions can be made when one third of an outbreak has been measured". As a result, if data were available that may assist in identifying the earliest onset of disease, in addition to any factors that may relate to pathogen mutation, more complicated yet more predictive models might become more accurate.

Detecting Viral Pathogens in Near Real Time

Computational software promises to help stem the spread of disease that can decimate civilian populations, and incapacitate military forces. Because of the time constant between when an individual becomes exposed and infected to an airborne pathogen such as influenza, and when that individual becomes symptomatic may be many days (1-4 day incubation period), vector transmission to other persons will likely have occurred. Only a small fraction, generally the very young or the very old, in the early stages, will end up in a hospital or clinic where positive identification of the virus has been obtained and is available as a statistic. Being able to monitor the level of viral load in a local population outside of the hospital or clinic setting, coupled with an ability to know precisely what the genome sequence of the virus is, would advance the state-of-the-art in epidemic predictive capability substantially. We believe we may be able to achieve this goal through the merging of several well-established technologies, and the combination of several new developments in gene sequencing.

Influenza, as well as many bacterial agents, can survive for hours as an airborne species. Because droplets from a cough or sneeze encapsulate many virions, the probability for disease transmission in congested public areas is very high. In general, particles that are between less than 5 microns can remain airborne for many hours and the smaller the particulate, the longer the residence time. As a mucosal enveloped packet of virions moves through the air, evaporation of water (90% water, 0.5-5% high molecular weight glycoproteins) causes the droplet to become smaller and thus more mobile. Residence time is enhanced if the humidity level is high, and if there is a lack of direct sunlight. The research lab of Dr. Bourouiba at MIT has investigated the fluid dynamics of disease transmission[1], and has determined experimentally that cough ejecta and sneeze cloud last typically approximately 250 milliseconds can literally shoot across a room in a matter of seconds, 200 times farther than previously thought.

[1] https://lbourouiba.mit.edu/

"Emerging or reemerging viral and bacterial infectious diseases (e.g. H1N1, H5N1, SARS, tuberculosis) have increasingly high human and economic consequences (IMF/ World Bank 2006). Confined environments, such as airplanes, hospitals and schools, serve as mixers where pathogens can stay suspended and spread from host to host. Hence, understanding the dynamics of pathogens indoors is critical to improving the modeling and control of epidemics (Settles 2006; Tang et al. 2006; Weber & Stilianakis 2008). Nevertheless, the transmission mechanisms of even the most common respiratory diseases remain poorly understood. Three modes of transmission are discussed in the medical literature. Self-inoculation may arise through direct contact with the mucus (or other bodily fluids) of an infectious subject. Large droplet transmission may arise through the spraying of infected droplets directly onto the conjunctiva or mucus of a susceptible host via coughing or sneezing. Airborne transmission may arise through inhalation of relatively small infected droplets or the pathogen-bearing solid residues of size <5-10 μm, referred to as droplet nuclei, that can form from the small droplets via evaporation (e.g. Nicas, Nazaroff, & Hubbard 2005; Tellier 2006). The first two modes are termed direct short-range routes of pathogen transmission, both requiring the close proximity of individuals, while the third is an indirect long-range route of transmission. Violent expirations release multiphase turbulent flows that are generally composed of buoyant hot moist air and suspended droplets of various sizes. These droplets contain components such as pathogens and minerals that can form droplet nuclei after evaporation of the drop's liquid phase. At low Reynolds number, the Stokes settling speed $U_S = gd^2/(18\mu)(\rho_d - \rho)$ of a droplet of diameter d and density $\rho_d$ in an ambient gas phase of density $\rho$ is proportional to its surface area which necessarily decreases with time due to evaporation". As a result, such ejecta can remain airborne and viable far longer than previously believed.

Given the high airborne viral load that exists in congested public spaces, it would seem natural to seek out such spaces to place a viral air sampler. The goal of such a sampler would be to sample trace species indicative of viral agents, concentrate such species to a level of at least 200 nano grams or better, and subject the viral species to continuous genomic sequencing. The viral concentration and sequence data ideally could then be uploaded to the 'cloud', for deterministic computer modeling that merges the data with other variables previously described, such as PAHO, weather, and social media input variables. The added advantage of the sequencing functionality is that emergent strains can be revealed in an almost near real-time fashion even before a patient-vector becomes symptomatic. An added benefit is that many patients who are symptomatic may never seek professional medical attention, and thus never end up as a PAHO data point. A distribution of automated viral air samplers worldwide, seeded in locations such as airports and train stations, could provide data never previously attainable in epidemiology.

Air Sampling for Pathogens

The proposed system is comprised of several key parts necessary to sample ambient air laden with target pathogens. The entrance to the air sampler utilizes a common aerosol impaction filtration method. High velocity air is channeled around a 90-degree bend, causing heavier fractions to impact and embed in the end channel. Soft media such as low vapor pressure grease allow heavy fraction to be permanently entrained. As lighter fractions negotiate the change in direction, subsequently smaller and smaller fractions can be derived through the stratification based on mass through the airflow. At a suitable point downstream, a cross current electrospray source is employed to nondestructively capture bioaerosols from the air flow, and remove them from the air stream via electrostatic forces. To employ electrostatic separation, the bioaerosols are nondestructively ionized using a process known as 'electrospray'. Electrospray is a the process by which a conductive fluid, in this case an aqueous solution, is utilized to produce a nanospray of desorbing droplets which attract and capture polar or polarizable species from the air, of which virions are a part. (The ability to non-destructively ionize a virus has been well reported in the literature, where electrospray air capture of polar and polarizable species was accidentally discovered by Fenn et al at Yale in 1984, where the author was a research student. Fenn was awarded the 2002 Nobel Prize in Chemistry for Electrospray mass Spectroscopy). As a charged species, final filtration is accomplished using an electrostatic filter, similar to those found on magnetic sector mass spectrometers. Preliminary identification and separation of the virion or biospecies can be achieved preferably using charge-detection mass spectrometry.

SUMMARY

The disclosed invention provides a means to perform both surveillance and forecast of public health and force protection pathogen threats, and specifically, viral outbreaks. The enabling tool for the achievement of these goals is the machine that will collect and analyze the captured viruses. Then, predictions, feedbacks and control measures can inhibit the evolution of an outbreak assuming that there are the means and the will to act. Having an almost real-time tool to measure viral load of air at condensed areas is an ideal situation for public policy makers since they could evaluate immediately and accurately the impact of a decision. A near real-time atmospheric viral/selective bioaerosol sampler and genetic sequencer is proposed. In many instances, an outbreak is caused by what is referred to as "patient zero", the person who is the original carrier of a specific disease. If the "patient zero" can be found more quickly, or at least "pathogen zero" found more quickly, government agencies such as the CDC (Centers for Disease Control) or WHO (World Health Organization) can quickly identify potential sources of new epidemics. While the proposed sampler obviously cannot identify a specific vector or patient-zero for a viral agent, the technology promises to yield previously unattainable data on the emergence and spread of new virulent agents. This information can also be utilized by pharmaceutical companies to create flu vaccines that are created for specific regions where a known type of pathogen exists, specific to that genome. By using this information, flu manufacturers will be less dependent essentially educated guesses at what type of pathogen is "out in the wild", so its effectiveness will be much greater, and production response time shortened considerably.

Reference may be made to the new so-called 'Cancer Moonshot' effort in the U.S. to address solving cancer riddles. Of all the recommendations from the research community thus far, none has been more dominant than utilizing the benefits of the virtual cloud. Cloud computing enables large-scale collaborative analysis. "Two of the 10 recommendations specifically call for a direct patient engagement network and the creation of adult (and pediatric) immunotherapy clinical trials networks. However, collaboration is at the core of all 10 recommendations, as the Blue Ribbon Panel unequivocally calls for better data sharing. The scale of the data used in cancer discovery means computation has a huge role in supporting research. Every sequenced genome requires 300-400 GB of hard disk space just to store the raw and processed files. By 2025, the amount of human genomic data is predicted to be 2-40 exabytes, exceeding the storage requirements of astronomy and YouTube. To overcome these challenges, the cancer research community is increasingly turning to the cloud to store and analyze cancer genomic data. The U.S. National Cancer Institute (NCI) initiated Cancer Genomics Cloud Pilots to enable researchers to access The Cancer Genome Atlas (TCGA)—the world's largest public genomic data set—containing over 2 petabytes of sequencing and other data from more than 11,000 patients. Rather than waiting weeks to download the data, researchers can log in to a cloud-based system to explore the data and run large-scale analyses. A key value of the cloud is that collaboration is default; researchers can log in to the NCI Pilots from anywhere in the world and work together on a project".

In the proposed final configuration, distributed viral air samplers will be 'seeded' in areas of human congestion, such as airports and other mass transit locations around the world. Ambient air will be continuously drawn into the sampler, and larger fractions filtered out until only specific bio-aerosols are left. These bio-aerosols, specifically of interest influenza virions, become charged ions after interaction with an electrospray source. Using a combination of electrostatic filtration and charge detection spectrometry, target virions are accumulated and subjected to continuous genetic sequencing via an Oxford Nanoprobe analyzer or other suitable sequencer. The viral (or other bioaerosol of interest) concentration and genetic sequence data is uploaded via sampler internal telemetry to the cloud via RF or broadband internet connectivity. The data collected by these 'bio-nodes' is then used as part of an improved probability algorithm for predicting the outbreak of a given viral strain in a given region, and for worldwide infectious disease monitoring. The successful implementation of the proposed technology could be to epidemiology what GPS has meant to navigation in its impact on humanity.

OVERVIEW OF THE INVENTION

Detecting Viral Pathogens in Near Real Time:

Computational software promises to help stem the spread of disease that can decimate civilian populations, and incapacitate military forces. Because of the time constant between when an individual becomes exposed and infected to an airborne pathogen such as influenza, and when that individual becomes symptomatic may be many days (1-4 day incubation period), vector transmission to other persons will likely have occurred. Only a small fraction, generally the very young or the very old, in the early stages, will end up in a hospital or clinic where positive identification of the virus has been obtained and is available as a statistic. Being able to monitor the level of viral load in a local population outside of the hospital or clinic setting, coupled with an ability to know precisely what the genome sequence of the virus is, would advance the state-of-the-art in epidemic predictive capability substantially. We believe we may be able to achieve this goal through the merging of several well-established technologies, and the combination of several new developments in gene sequencing.

Influenza, as well as many bacterial agents, can survive for hours as an airborne species. Because droplets from a cough or sneeze encapsulate many virions, the probability for disease transmission in congested public areas is very high. In general, particles that are between less than 5 microns can remain airborne for many hours and the smaller the particulate, the longer the residence time. As a mucosal enveloped packet of virions moves through the air, evaporation of water (90% water, 0.5-5% high molecular weight glycoproteins) causes the droplet to become smaller and thus more mobile. Residence time is enhanced if the humidity level is high, and if there is a lack of direct sunlight. The research lab of Dr. Bourouiba at MIT has investigated the fluid dynamics of disease transmission, and has determined experimentally that cough ejecta and sneeze cloud last typically approximately 250 milliseconds can literally shoot across a room in a matter of seconds, 200 times farther than previously thought.

Emerging or reemerging viral and bacterial infectious diseases (e.g. H1N1, H5N1, SARS, tuberculosis) have increasingly high human and economic consequences (IMF/World Bank 2006). Confined environments, such as airplanes, hospitals and schools, serve as mixers where pathogens can stay suspended and spread from host to host. Hence, understanding the dynamics of pathogens indoors is critical to improving the modeling and control of epidemics (Settles 2006; Tang et al. 2006; Weber & Stilianakis 2008). Nevertheless, the transmission mechanisms of even the most common respiratory diseases remain poorly understood. Three modes of transmission are discussed in the medical literature. Self-inoculation may arise through direct contact with the mucus (or other bodily fluids) of an infectious subject. Large droplet transmission may arise through the spraying of infected droplets directly onto the conjunctiva or mucus of a susceptible host via coughing or sneezing. Airborne transmission may arise through inhalation of relatively small infected droplets or the pathogen-bearing solid residues of size <5-10 μm, referred to as droplet nuclei, that can form from the small droplets via evaporation (e.g. Nicas, Nazaroff, & Hubbard 2005; Tellier 2006). The first two modes are termed direct short-range routes of pathogen transmission, both requiring the close proximity of individuals, while the third is an indirect long-range route of transmission. Violent expirations release multiphase turbulent flows that are generally composed of buoyant hot moist air and suspended droplets of various sizes. These droplets contain components such as pathogens and minerals that can form droplet nuclei after evaporation of the drop's liquid phase. At low Reynolds number, the Stokes settling speed $U_S = gd^2/(18\mu)(\rho_d-\rho)$ of a droplet of diameter d and density $\rho_d$ in an ambient gas phase of density $\rho$ is proportional to its surface area which necessarily decreases with time due to evaporation. As a result, such ejecta can remain airborne and viable far longer than previously believed.

Given the high airborne viral load that exists in congested public spaces, it would seem natural to seek out such spaces to place a viral air sampler. The goal of such a sampler would be to sample trace species indicative of viral agents, concentrate such species to a level of at least 200 nano grams or better, and subject the viral species to continuous genomic sequencing. The viral concentration and sequence data ideally could then be uploaded to the 'cloud', for deterministic computer modeling that merges the data with other variables previously described, such as PAHO, weather, and social media input variables. The added advantage of the sequencing functionality is that emergent strains can be revealed in an almost near real-time fashion even before a patient-vector becomes symptomatic. An added benefit is that many patients who are symptomatic may never seek professional medical attention, and thus never end up as a PAHO data point. A distribution of automated viral air samplers worldwide, seeded in locations such as airports and train stations, could provide data never previously attainable in epidemiology.

Air Sampling for Pathogens

The proposed system is comprised of several key parts necessary to sample ambient air laden with target pathogens. The entrance to the air sampler utilizes a common aerosol impaction filtration method. High velocity air is channeled around a 90-degree bend, causing heavier fractions to impact and embed in the end channel. Soft media such as low vapor pressure grease allow heavy fraction to be permanently entrained. As lighter fractions negotiate the change in direction, subsequently smaller and smaller fractions can be derived through the stratification based on mass through the airflow. At a suitable point downstream, a cross current electrospray source is employed to nondestructively capture bioaerosols from the air flow, and remove them from the air stream via electrostatic forces. To employ electrostatic separation, the bioaerosols are nondestructively ionized using a process known as 'electrospray'. Electrospray is a the process by which a conductive fluid, in this case an aqueous solution, is utilized to produce a nanospray of desorbing droplets which attract and capture polar or polarizable species from the air, of which virions are a part. (The ability to non-destructively ionize a virus has been well reported in the literature, where electrospray air capture of polar and polarizable species was accidentally discovered by Fenn et al at Yale in 1984, where the author was a research student. Fenn was awarded the 2002 Nobel Prize in Chemistry for Electrospray mass Spectroscopy). As a charged species, final filtration is accomplished using an electrostatic filter, similar to those found on magnetic sector mass spectrometers. Preliminary identification and separation of the virion or biospecies can be achieved preferably using charge-detection mass spectrometry.

Once the virions have been selected, they are accumulated on a 'witness plate', in preparation for automated sequencing. The sequencer of choice is a nano-pore-device, The Nanopore system employs a bespoke, proprietary pore-forming proteins to create pores in membranes. Pore-forming proteins are common in nature. For example, the protein α-hemolysin and similar protein pores are found naturally in cell membranes, where they act as channels for ions or molecules to be transported in and out of cells. A protein nanoporea-hemolysin is a heptameric protein pore with an inner diameter of 1 nm, about 100,000 times smaller than that of a human hair. This diameter is the same scale as many single molecules, including DNA. In a nanopore DNA sequencing, the system may process the sample until a minimum of tenfold read coverage over specified regions of interest has been seen, until a specific mutation has been observed in a sample or until enough sequence data has been collected to reliably assemble a sample against a reference. As DNA/RNA moves through the pore, changes in electric potential are translated into genetic sequence data. After electrospray charging and sorting if incoming virions and subsequent lysing, the process then is concentrate, extract, genetic library prep, and continuous flow sequencing. Regardless of the genetic sequencer employed, the electrospray capture and pathogen selection concept is adaptable to any subsequent downstream analytical tool. The electrospray capture technology has been proven and applied to biowarfare agent capture under prior Navy, Marine Corps, and National Academy of Science support. In addition, the technology was featured in a NASA Tech Briefs edition in 2011 after application on a spacecraft air filtration system contract that included John Fenn and former astronaut Dr. Buzz Aldrin.

How Electrospray Air Capture Works

During World War I, John Zeleny did some experiments in which he passed a low flow of conducting liquid through a metal capillary tube or "needle" maintained at high potential relative to an opposing counter-electrode. The resulting intense field at the needle tip dispersed the emerging liquid into a fine spray of highly charged droplets. Zeleny also noted that as the droplets evaporated they became unstable and disrupted into a multiplicity of smaller droplets. Such instability had been predicted and characterized by Lord Rayleigh in 1883. He argued that evaporation of solvent would increase the surface charge density on the droplet until Coulomb repulsion would overcome the surface tension that held the droplet together. As the electrical potential between the source (needle or wick) is increased, the electrical attraction slowly overcomes the surface tension of the fluid and a cone is formed from which emerges a jet of fluid at the apex of that cone. This cone is called a "Taylor Cone" after Sir Geoffrey Taylor. This jet of fluid then breaks up into a plurality of droplets. The resulting "Rayleigh Instability" (like charges that repel one another) would disrupt the droplets into a multiplicity of yet smaller droplets.

In the early 1980's, John Fenn and his colleagues at Yale used this approach and added a counter-current bath gas of nitrogen, which forced the evaporation of the solvent, which contained the analyte-solute in the solvent of the spray. Repeated fissioning of the discrete droplets yields a single gas phase ion with multiple electrical charges. When introduced into a mass spectrometer, the masses of biomolecular proteins and even living intact viruses can be ascertained. Analytes must be a charged species or intact ion in order to be manipulated and detected by a mass analyzer. Prior to this, analytes typical of a biomedical nature would fragment or dissociate by other ionization methods. It is the revolutionary nature of electrospray that gave rise to the study of the field now known as "Proteomics" and where Fenn's contribution was recognized through the award of the Nobel Prize in Chemistry in 2002 mentioned earlier. Fenn reported for the first time intact ions of proteins and peptides and moreover, because of their multiple charges, the mass/charge ratios of those ions were greater than ever obtained in the past using any type of mass spectrometer.

It is appropriate to note the reasons for transforming neutral pathogens into charged ions before attempting characterization. They include (1) The ability to control the trajectories and destinations of charged species by appropriate combinations of electric and magnetic fields and (2) A detectability that is generally much greater for ions than for neutral species because each ion gives rise to at least one electron in a primary signal current that can be greatly amplified by well known techniques. Moreover, ion-electron multipliers can produce millions of electrons in signal current for each incident ion. It is also appropriate to comment on how sensitivity is best expressed, i.e. in what units? In chromatography, perhaps the most widely used of all analytical techniques, a specific quantity of analyte is injected into a flow of mobile phase entering a separation column. Sensitivity is thus defined in terms of the smallest amount of injected analyte, e.g. in pico-grams or pico-moles that will give rise to a distinguishable peak in the effluent. Sensitivity defined in this way is not very meaningful in applications where one wants to know the concentration of some species in a gas or liquid of interest or whether a particular species is present in that gas or liquid when the available quantity of that gas or liquid may be large relative the quantity required for the analytical procedure. In such cases the appropriate measure of sensitivity is the lowest concentration of analyte in a sample liquid or gas at which detection and identification can be achieved. This minimum detectable concentration is clearly a relevant measure of sensitivity in a search for, say, a toxic chemical species, by analyzing a stream of air from a region where they might be concealed. Unfortunately, much if not most of the available data on detection of explosives and chemical or biological warfare agents is reported in minimum detectable amounts rather than minimum detectable concentration. Results in terms of the former cannot be meaningfully translated into the units of the latter.

The inventor and his colleagues at Yale under John Fenn discovered that electrospray ionization, now traditionally used for mass spectrometry, has the ability to "getter" or capture polar or polarizable trace species from the air, of which bio-species are a part. Since 9/11, there has been a flurry of development of many new methods and devices to identify potentially toxic agents of all kinds. But what seems to be missing is the fact that one needs to capture enough of the target species in order to achieve detection. Dr. Fenn (2002 Nobel Prize Chemistry) one stated that the sensors should not be called detectors, but "identifiers", and that a "detector" is really composed of a collection device and an identifier. If we collect more analyte from the surrounding air-diluent, we need a less sensitive identifier and vice-versa. Even better if the collection device captures and concentrates only the class of materials of interest while ignoring the background. It should be mentioned that the process allows for non-destructive capture of all airborne pathogens, including spores, bacteria, and viruses out of the ambient air.

DETAILED DESCRIPTION OF THE INVENTION

Charge Detection & Filtration of Specific Virions:

Electrospray has been demonstrated to non-destructively add charge to biological species, such as spores, bacteria, and viruses. Viruses that have been charged using electrospray have been shown to be capable of being coarsely separated from an air steam. So what do we do next to identify viruses that have been separated in an airstream? A way is needed to further filter virion particles, and concentrate them onto a surface for subsequent genetic sequencing.

For over three decades since John Fenn's discovery at Yale, electrospray ionization (ESI) has been used to ionize non-covalent complexes and subsequently transfer the intact ion into the gas phase for mass spectrometry (MS) analysis. ESI generates a distribution of multiple charged ions, resulting in a m/z spectrum comprised of a series of peaks, known as a charge state envelope. To obtain mass information, the number of charges for each peak must be deduced. For smaller biological analytes like peptides, the charge states are sufficiently resolved and this process is straightforward. For macromolecular complexes exceeding ~100 kDa, this process is complicated by the broadening and shifting of charge states due to incomplete desolvation, salt adduction, and inherent mass heterogeneity. As the analyte mass approaches the MDa regime, the m/z spectrum is often comprised of a broad distribution of unresolved charge states. In such cases, mass determination is precluded. Charge Detection Mass Spectrometry (CDMS) is an emerging MS technique for determining the masses of heterogeneous, macromolecular complexes. In CDMS, the m/z and z of single ions are measured concurrently so that mass is easily calculated. With this approach, deconvolution of a m/z spectrum is unnecessary. This measurement is carried out by passing macroions through a conductive cylinder. The induced image charge on the cylindrical detector provides information about m/z and z: the m/z is related to its time-of-flight through the detector, and the z is related to the intensity of the image charge. As a result, given the megadalton masses of many viruses (Influenza average value was $174\times10^6$ daltons), the application of charge detection spectrometric techniques is appropriate to the present tasking.

As electrospray charged virions are sampled away from the aerosol pre-filter, an image charge will be produced each time a virus particle passes through the flight tube, FIG. 3. Therefore, a viral count can be obtained (analogous to blood cell counts in a Coulter counter), in addition to m/z charge spectral information about the specific virion selected. Knowing the mass and the viral counts, the quantity of viral particles can be deduced as collected on the witness plate or analysis target inside the CDMS system. Deposition on the discharge or witness plate is the last step before introduction to the genetic sequencer, if the target is not the sequencer itself. Being charged species, an electrostatic gating system may be created where arriving viral particles can be alternately introduced into the genetic sequencer front end, or discharged and collected for subsequent study, or destroyed as desired.

It should be noted that inventive claims extend to charge detection spectometry performed at or near atmospheric pressure. In addition, ion mobility may be substituted for charge detection spectrometry at or near atmospheric pressure for charged bio-species sorting subsequent to preferred nanopore identification.

Viral Lysis

Several lysis methods may be employed in the sampler. Traditional reagent-thermal based methods may be employed, or, a reagentless electrical lysis approach may be employed, which has been demonstrated for vaccinia virions. Using a pair of nano electrodes, an externally applied electric field produces the trans-membrane potential, and it generates electric field inside the lipid bilayer membrane. This internal electric field generates a Maxwell stress, compressing the membrane in the normal direction, and rupture the membrane if the electric field is above critical value. Electric lysis is virtually instantaneous, whereas traditional reagent based approaches require up to 30-45 minutes per sample.

One aspect of standard reagent lysis is the fact that the process is performed using aqueous fluids at atmospheric pressure. In ESI-MS and ESI-CDMS, the collected species will be subjected to a partial pressure region, where aqueous fluids would instantaneously evaporate. One solution to low pressure viral lysis, aside from the aforementioned electric field method, is the use of ionic liquids, which have recently been shown to not only lyse virion capsids, but do so in some cases at higher efficiency than commercial reagent kits. Ionic liquids are room temperature salts, which have essentially zero vapor pressure. In addition, ionic liquids may serve an added purpose in helping perform genetic sequencing, discussed in the section on improved nanopore sequencing.

Sequencing

Virions in the airstream, once ionized by electrospray, filtered and sequestered based on mass and charge information, are now ready for sequencing. As indicated earlier, the preferred sequencing device is a graphene nanopore system, although any sequencer could in theory be utilized. A graphene nanopore device deduces genetic sequences based on an ionic current through a set of nano sized voids or pores, and measures the changes in current as biological molecules pass through the pore or near it. The information about the change in current can be used to identify that molecule compared to a library. A nanopore can be thought of as a genetic Coulter counter, referring to the idea of blood cell counts through a capillary in the presence of a conductive electrolyte, coupled to a pico-ammeter to measure the pulses.

The most significant advantage of a nanopore system aside from its small size and speed, however, is the lack of need for PCR amplification, as only 200 ng or less of viral material is required for analysis. As a strand of DNA is passed through a nanopore, the current is changed as the bases G, A, T and C pass through the void in different combinations. In addition, the system is the ability to continuously sample material.

Graphene sheets are now being tested by several investigators, that improve both the resolution and speed in which nucleotide sequences can be sampled using nanopore technology. This will allow sampler reduced in size and higher sensitivity of the sequencer to incoming genomic samples.

Improved Nanopore Genetic Sequencing in Vacuo

Nanopore sequencing resolution can be improved by using graphene sheets in lieu of protein based nanopore structures. However, real-time DNA sequencing is currently a major challenge because longitudinal current detection cannot distinguish individual nucleotides due to the thickness of membrane (>10 bases) and the fast translocation of a single base[2]. In any nanopore system, an electrolyte is required to create an ion flow from one side of the pore to the other, dragging along the nucleotide strand with it. It is hereby proposed to use an ionic liquid as the electrolyte, or a silicone based diffusion pump oil seeded with an ionic liquid. The point of this approach is that the witness plate in the charge detection mass spectrometer can actually be the genetic sequencer in vacuo! In fact, it may be possible to create hundreds, if not thousands, of graphene nanopore sequencer 'cells', arranged in a matrix such that each cell can be selected for new genome sample processing depending on the desired type of virion being interrogated. The charged virions emitted from the charge detection mass spectrometric filter (we use the term charged particle as the virus is not an ion in the traditional sense), and electrostatically or magnetically deflected to the desired sequencing cell.

This concept can be envisioned as a charged species equivalent to the old style cathode ray tubes used in early televisions and computer monitors. In those devices, an electron beam was continually deflected and scanned across a phosphor-coated screen to complete a raster. Similarly, one can deflect charged virions to any desired target for immediate analysis or sequesterization for subsequent laboratory study.

Improved Nanopore Nucleic Acid Sequence Correlation

One issue with nanopore genetic sequencing is that the nucleic acid strand passes through the pore very quickly, such that the resulting charge fluctuation due to individual base pairs may not yield as sharp discrete steps as would be the case if the strand passed through the pore more slowly. This reduces current resolution and thus nucleic acid identification accuracy. At present, this is dealt with by repetitive scans that are averaged or correlated over time to produce the desired current change indicative of the target sequence. One possible solution to this problem is the use of alternating current or AC instead of a DC bias in the electrolyte solution across the nanopore. By varying the frequency, polarity, and duty cycle of the applied potential, the target strand can be repetitively moved back and forth through the nanopore, permitting the requisite iterative sweeps required for acceptable signal averaging in far less time than using DC.

BRIEF DESCRIPTION OF THE DRAWINGS

Reference Numerals

FIG. 1:
10 Represents a conductive fluid capable of electrospray operation which may be volatile or non-volatile
20 Denotes a needle or tube or capillary for containing and supporting an electrospray
30 Is a Taylor Cone
40 Is a jet of fluid from an electropsray
50 is a dispersion of electrospray droplets
60 represents the coulomb explosion of electrospray droplets
70 represents desorbing electrospray droplets
80 represents bio-aerosol species in air being attracted to desorbing electrospray droplets
90 is a collection plate or witness plate for collection of charged bio species
100 is a collection plate or surface that is preferably a nanopore target
110 represents a power supply providing an electrical potential sufficient to yield a Taylor Cone from a needle or capillary 20 or paperspray source
FIG. 2:
40 represents an electrospray source in totality encompassing elements 20,30,40, and 110 from FIG. 1
80 represents incoming ambient bioaerosols just before contact with electrospray droplets as in reference 80
120 is a capillary tube
130 are skimmers used to streamline the incoming charged species into a singular beam or linear stream of charged species
140 is an image charge detector tube
150 is a collection plate or target
160 is a picoammeter coupled to analysis device such as a computer
FIG. 3:
170 Is a power supply for creating a difference of potential on either side of a nanopore
180 represents a strand of DNA, RNA, or any nucleotide sequence, or a protein or other biological molecule
190 is a nanopore, preferably in a sheet of graphene
200 is an electrolyte solution
FIG. 4:
80 represents a strand of DNA, RNA, or any nucleotide sequence, or a protein or other biological molecule
200 is an electrolyte solution
FIG. 5:
210 is a diagram of a cathode ray tube
220 is a diagram of a charged particle delivery system
230 is the sample inlet
240 is an electrospray source
250 is an electrostatic focusing system for the electrospray
260 represents horizontal electrostatic deflection plates
270 represents vertical electrostatic deflection plates
280 represents a nanopore detection target
290 represents a beam of charged bio-species, such as organic ions, viruses, bacteria, prion, protein, or nucleic acid
FIG. 6:
300 Denotes the starting point of one scan preferred raster scanning of charged bio-species into well targets for preferred nanopore analysis
310 Denotes the end point of one scan preferred raster scanning of charged bio-species into well targets for preferred nanopore analysis FIG. 7:
320 Denotes ambient air laden with bio-aerosol species sample introduction
330 Denotes 1$^{st}$ stage heavy fraction filtration
340 Denotes electrospray charging of ambient bio aerosol species
350 Denotes second stage electrostatic filtration of bio species
360 Denotes charge detection mass spectroscopy and gating electrodes
370 Denotes lysing, extraction, and nanoporesequencing
380 Denotes data extraction step
390 Denotes Data transmission or migration to data cloud, internet, or network
400 Denotes application of predictive modeling algorithm

DETAILED DESCRIPTION OF DRAWINGS

Figure 1:
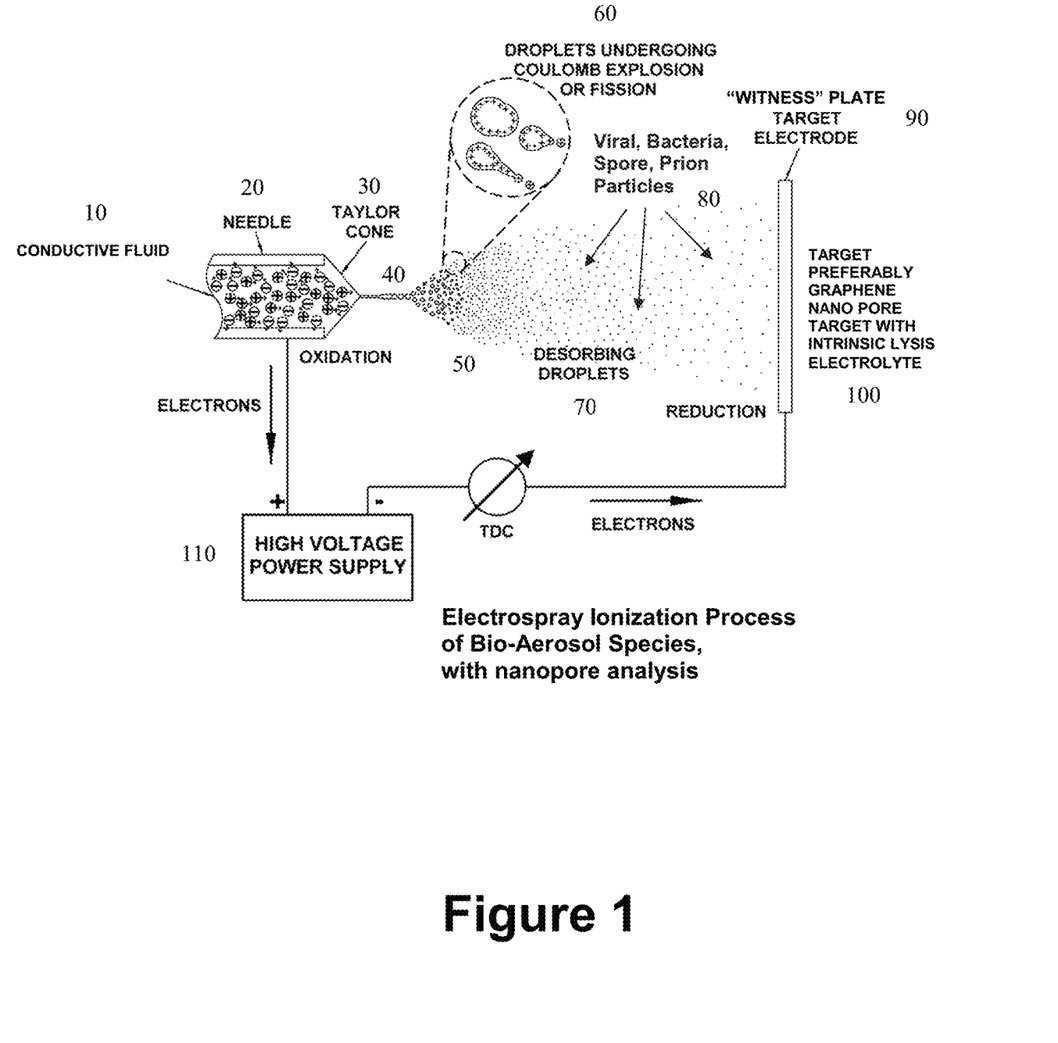

FIG. 1 is a diagram of the electrospray capture process for biological trace species from the air. The process begins with the introduction of a conductive fluid driven by either capillary action or hydrostatic force into an electrically conductive needle 20, where a difference of electric potential is applied between the needle 20 and a target 90 using a power supply 110 capable of creating a Taylor Cone 30 from which emerges a jet of fluid 40 which as the fluid evaporates 50, results in desorbing droplets 70, said droplets carrying a surface charge such that ambient biological species 80 are attracted and absorbed by aforementioned desorbing droplets 60, until only charged biological trace species remain and are deposited onto the opposing electrical pole target 90, which is preferably a graphene nanopore with an electrolyte on either face, said electrolyte preferably being a low volatility ionic liquid that will not evaporate under any level of vacuum, to which a difference of electrical potential has been applied.

Figure 2:
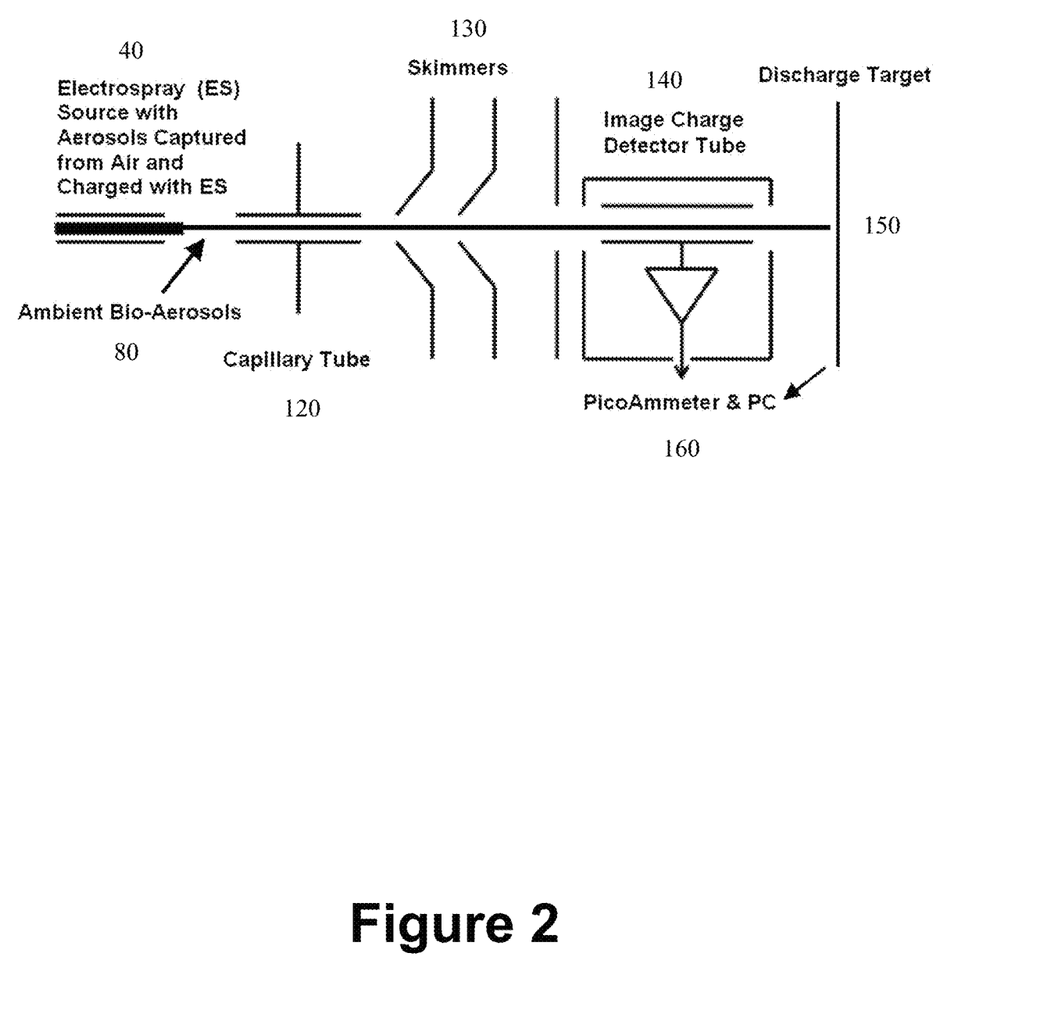

FIG. 2 illustrates the preferred embodiment of the invention, a charge detection mass spectrometer with a target that consists of a nanopore detector 150. The electrospray source 40 emits desorbing electrospray droplets to which ambient polar or polarizable biological trace species in the air are attracted 80 and absorbed by the droplets, resulting in discrete charged particles. The charged biological particles pass through a capillary tube 120 and into a succession of progressively pumped regions separated by skimmers 130 and through an image charge detector tube 140, said image charge of charged biological trace species being detected and amplified by a picoammeter and computer 160, before encountering end target 150 that is preferably a nanopore device capable of both lysing biological trace species and allowing a charge fluctuation of nucleic acid or other biological molecular group to pass through said nanopore, allowing identification of each molecular or atomic group or species.

Figure 3:
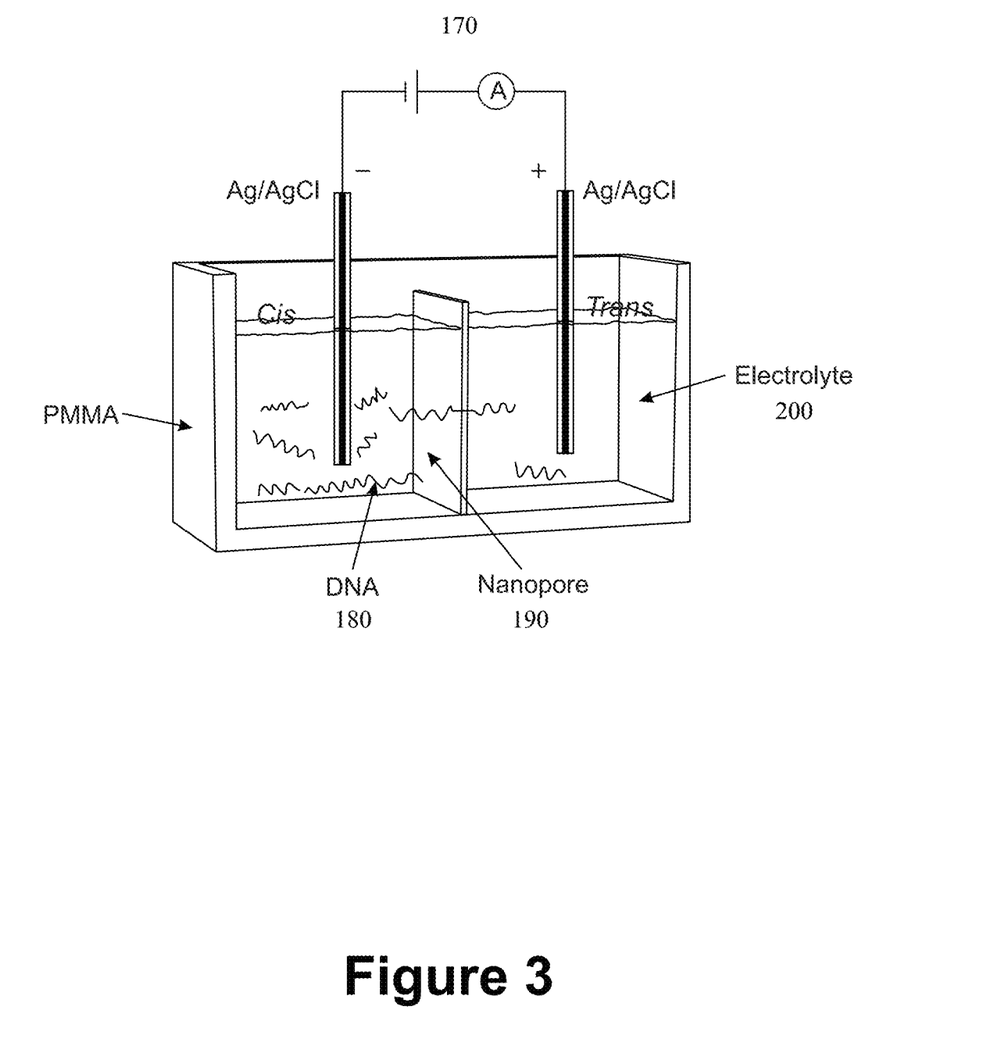

FIG. 3 discloses a nanopore nucleotide detection configuration. The nanopore, preferably a nano scale hole through a graphene sheet 190, where an electrolyte 200 is in contact with on either side, whereby a difference of potential 170 has been applied, such that a biological molecule, preferably a nucleotide sequence such as DNA 180, can be driven by ionic flow and pass through the aforementioned nanopore 190.

Figure 4:
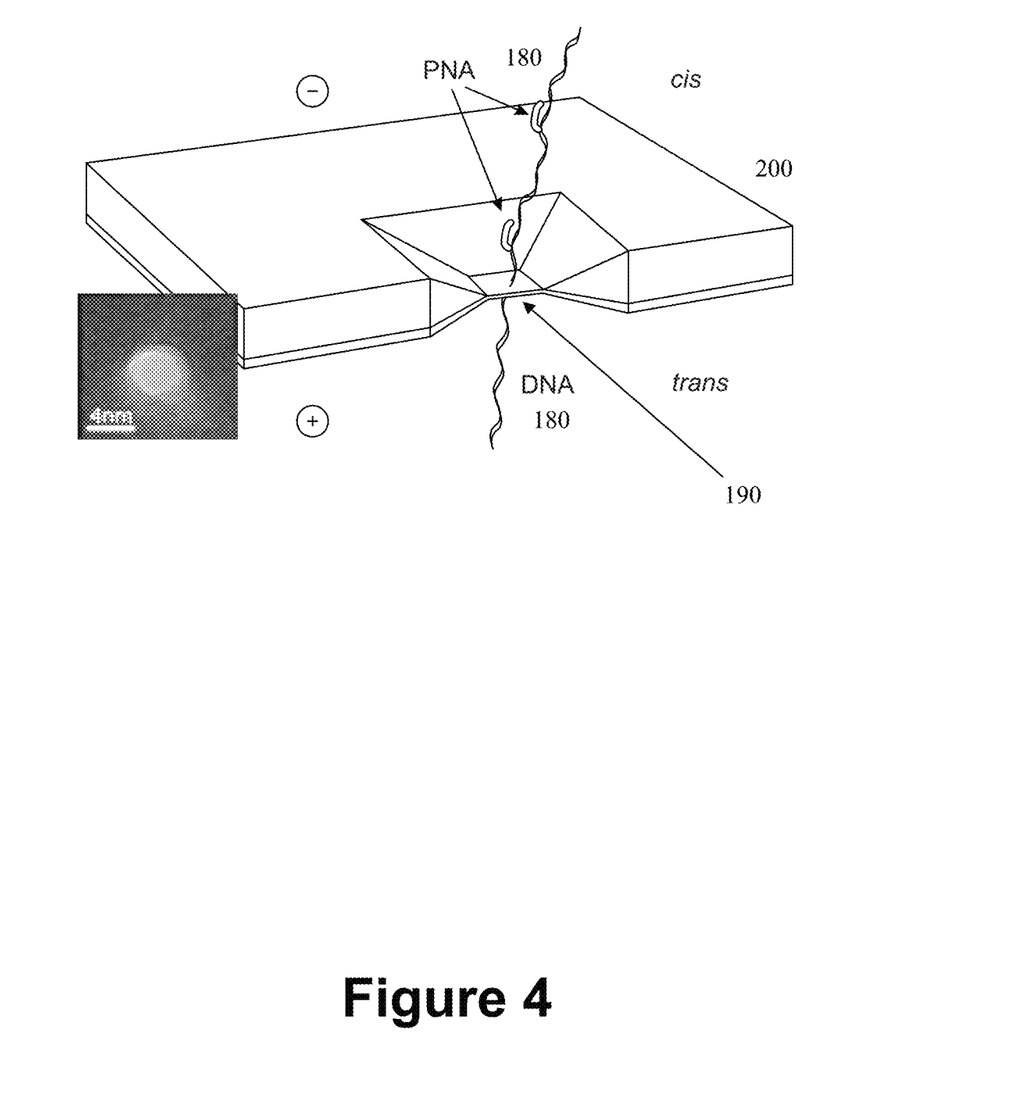

FIG. 4 is a close up picture of a graphene nanopore 190 where a nucleotide sequence such as DNA 180 can pass through said nanopore 190, so driven by the flow of ions in an electrolyte solution in contact with both sides of the graphene sheet, insulated by a dielectric 200 from both sides of the nanopore.

Figure 5:
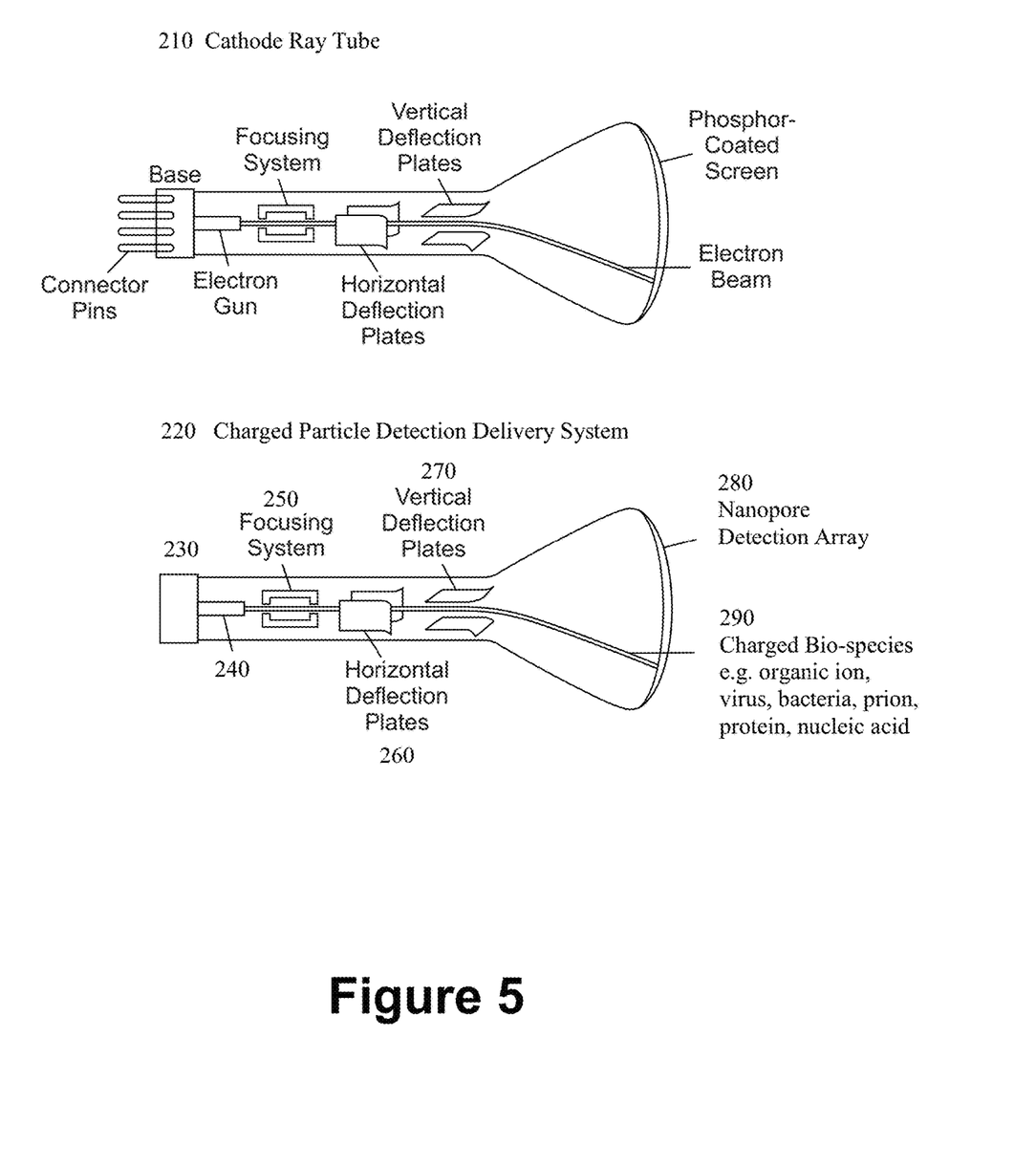

FIG. 5 is of two devices, a charged particle delivery system 220, and a cathode ray tube or CRT 210, upon which it is based. In a CRT, an electron gun emits electrons from a heated filament, which are electrostatically focused and then deflected using electrostatic or electromagnetic means such that a scan of the phosphor coated screen can be scanned in a successive raster pattern. The phosphor screen illuminates in the visible spectrum when high energy electrons strike its surface.

In the preferred charged particle delivery system 220, electrospray charged bioaerosol trace species 230, devoid of solvent or aqueous solution and introduced into a preferably partial pressure region, passing through a charge detection mass spectrometer tube 240, are electrostatically focused 250, and then deflected by horizontal 260 and vertical 270 plates, and scanned in a raster pattern or simply directed to a specific target on a nanopore detection surface 280, said charged bio-aerosol consisting of particulates or virions or nucleic acid or bacteria, or protein or peptide or any biospecies 290.

Figure 6:
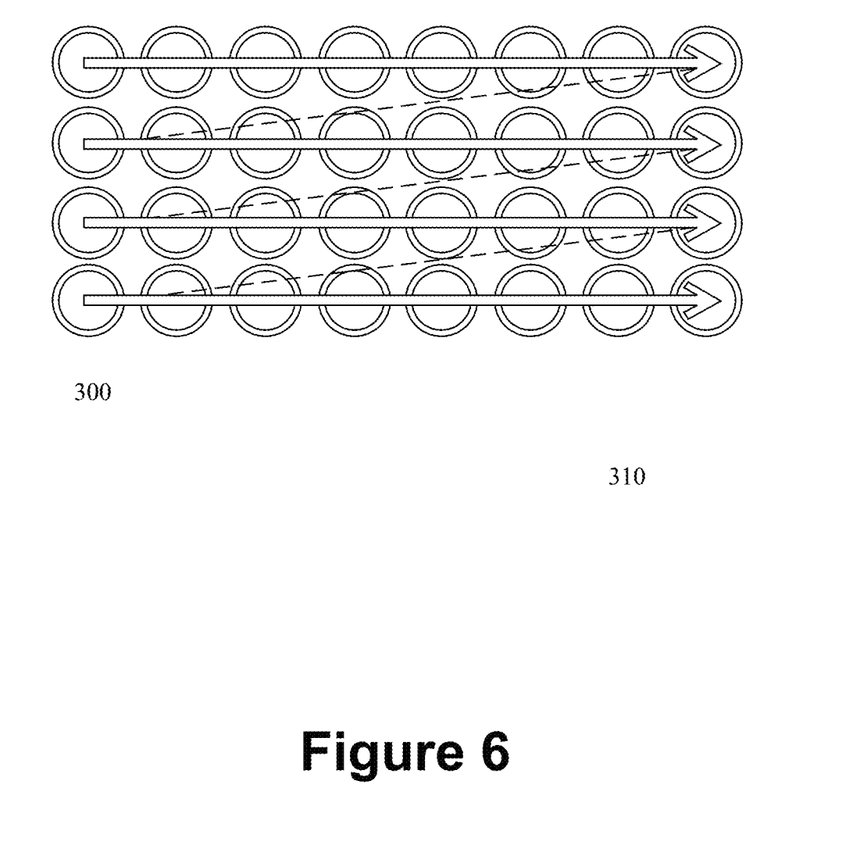

FIG. 6 is a raster pattern with a beginning point 300 and a terminal point 310, before the scan is retraced to the next level below or down next to and parallel to the preceding row of scan targets. Each target preferably represents an individual graphene ionic liquid nanopore well. Successive wells permit selective analysis depending upon the composition of the charge detection bio-particulate sample.

Figure 7:
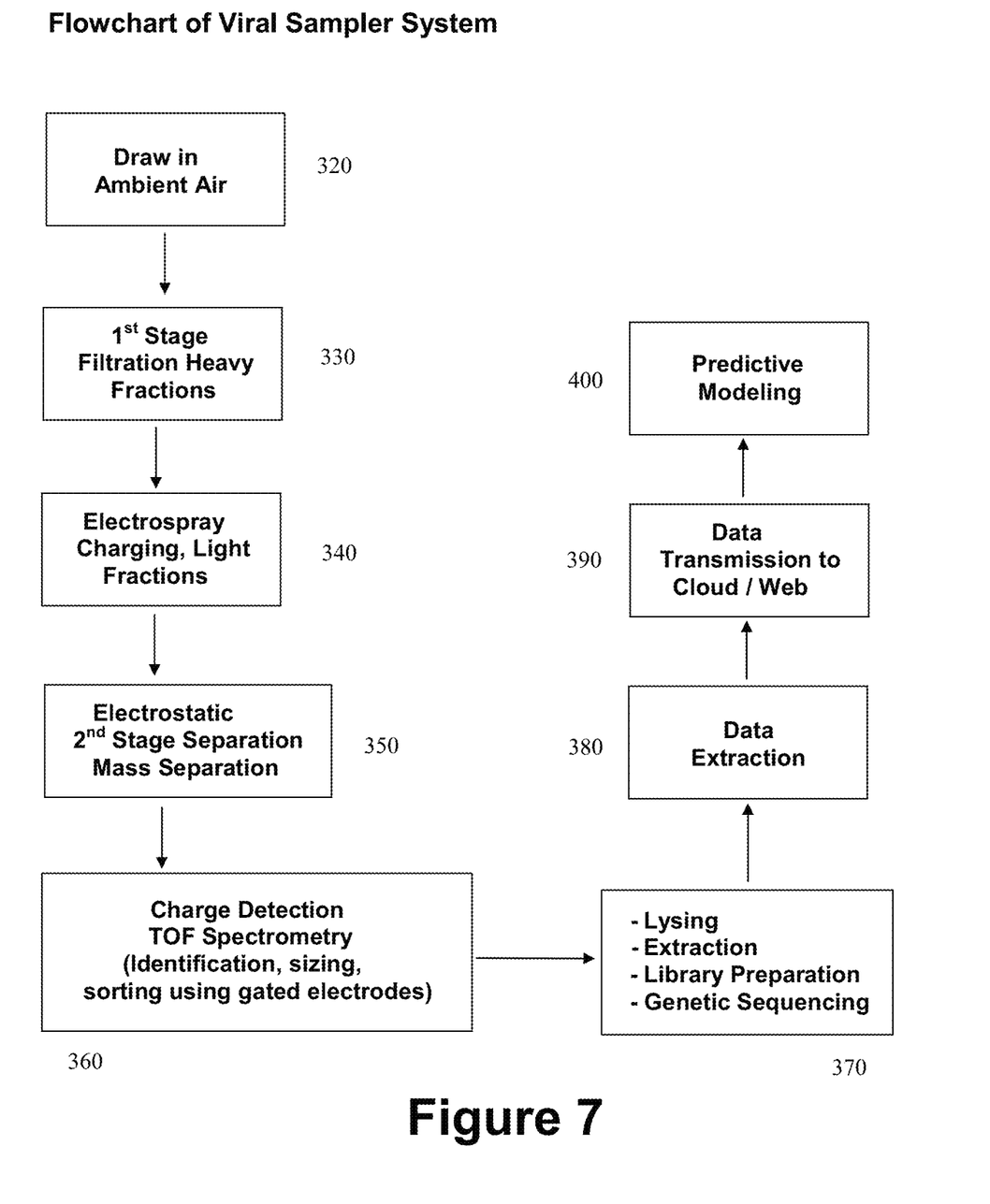

FIG. 7 is a flowchart of the preferred bio-aerosol and infectious agent air sampling system. Ambient air containing bio-species 320 is drawn in using a fan or other fluid movement device, where heavy fractions 330 are separated using aerosol separation techniques such as moving through a sharp bend. The bioaerosols are electrically charged after undergoing interactions with an electrospray plume 340. Electrostatic separation 350 further refines the charged particulates, Charge detection mass spectrometry provides charged bio-aerosol or pathogen image charge and m/z value, after which lysing, nucleic acid extraction, and genetic sequencing is performed 370, after which the fusion of data analysis and extraction 380 is performed, whereby said data is uploaded to the internet or cloud or other network 390, for subsequent predictive modeling 400.

What is claimed is:

1. A device to surveil and forecast public health and force protection pathogen threats, including viral outbreaks, the device comprising:
   (a) an air sampler utilizing aerosol impaction filtration, causing heavier fractions to impact and embed in an end channel, lighter fractions negotiating the change in direction, subsequently lighter fractions can be derived through a stratification based on mass through an airflow;
   (b) a cross current or counter current electrospray source employed to nondestructively capture bioaerosols from the air flow, and remove them from the air flow via electrostatic forces;
   (c) filtration accomplished using an electrostatic filter, preliminary identification and separation of a virion or a biospecies achieved using a charge detection mass spectrometer;
   (d) bioaerosols accumulated on a witness plate, in preparation for automated sequencing in a sequencer, the sequencer being a nanopore device, and the sequencer outputting a genetic sequence;

(e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected;

(f) an ionic liquid acting as an electrolyte in nanopore sequencer, or a silicone based diffusion pump oil seeded with an ionic liquid; and wherein the device is configured to perform a low pressure viral lysis via ionic liquids.

2. The device of claim 1, wherein the charge detection mass spectrometer comprises:

desorbing electrospray droplets to which ambient polar or polarizable biological trace species in the air are attracted, and absorbed by the droplets, resulting in discrete charged particles, a capillary tube configured to receive and pass through the charged biological particles into a succession of progressively pumped regions separated by skimmers and through an image charge detector tube;

a picoammeter and computer configured to detect and amplify the image charge of charged biological trace species;

a target that consists of a nanopore sequencer, the target configured to both lyse biological trace species and allow a charge fluctuation of nucleic acid or other biological molecular group to pass through the nanopore detector thereby identifying each molecular or atomic group or species thereof.

3. The device of claim 2, wherein the trace species are electrospray charged bioaerosol trace species, devoid of solvent or aqueous solution, and introduced into a preferably partial pressure region, passing through a charge detection mass spectrometer tube, electrostatically focused, deflected by horizontal and vertical plates, scanned in a raster pattern or simply directed to a specific target on a nanopore detection surface, said charged bioaerosol trace species consisting of particulates or virions or nucleic acid or bacteria, or protein or peptide or any bio-species.

4. The device of claim 3, wherein the charge detection mass spectrometer tube, and horizontal and vertical plates, are configured to scan the scanned in raster pattern in a successive raster pattern with a beginning point and a terminal point, before the raster pattern is retraced to the next level below or down next to and parallel to a preceding row of scan targets, each target represents an individual ionic liquid nanopore well, and successive wells permit selective analysis depending upon the composition of the electrospray charged bioaerosol trace species.

5. The device of claim 2, further comprising:

conductive fluid driven by either capillary action or hydrostatic force into an electrically conductive needle, where a difference of electric potential is applied between the needle and the target using a power supply configured to create a Taylor Cone from which emerges a jet of fluid which as the fluid evaporates, results in desorbing droplets, said droplets carrying a surface charge such that ambient biological species are attracted and absorbed by aforementioned desorbing droplets, until only charged biological trace species remain and are deposited onto an opposing electrical pole target, which is a nanopore with an electrolyte on either face, said electrolyte preferably being a low volatility ionic liquid that will not evaporate, to which a difference of electrical potential has been applied.

6. The device of claim 1, further comprising a low vapor pressure grease located in the air sampler utilizing aerosol impaction filtration and configured to allow heavy fraction to be permanently entrained.

7. The device of claim 1, wherein the charge detection mass spectrometer is configured to operate at or near atmospheric pressure.

8. The device of claim 1 further comprising:

an electrostatic gating system where arriving pathogen particles can be alternately introduced into the genetic sequencer, or discharged and collected for subsequent study, or destroyed as desired.

9. The device of claim 1, further comprising:

nanopore sequencer cells, arranged in a matrix such that each cell can be selected for new genome sample processing depending on the desired type of virion being interrogated, and wherein the charged virions emitted from the charge detection mass spectrometer and the charged virions are electrostatically or magnetically deflected to a desired sequencing cell.

10. The device of claim 1, wherein the sequencer is coated with a non volatile electrolyte.

11. The device of claim 10, wherein the non volatile electrolyte is ionic liquid.

12. The device of claim 1, wherein the sequencer is configured to upload the genetic sequence to a cloud computing network.

13. The device of claim 1, wherein the sequencer is configured to perform a comparative analysis of the genetic sequence a genetic sequence stored in a database.

14. A system to surveil and forecast public health and force protection pathogen threats, including viral outbreaks, the system comprising:

a first device comprising:

(a) an air sampler utilizing aerosol impaction filtration, causing heavier fractions to impact and embed in an end channel, lighter fractions negotiating the change in direction, subsequently lighter fractions can be derived through a stratification based on mass through an airflow;

(b) a cross current or counter current electrospray source employed to nondestructively capture bioaerosols from the air flow, and remove them from the air flow via electrostatic forces;

(c) filtration accomplished using an electrostatic filter, preliminary identification and separation of the virion or biospecies achieved using an ion mobility spectrometer;

(d) bioaerosols accumulated on a witness plate, in preparation for automated sequencing in a sequencer, the sequencer being a nanopore device, and the sequencer outputting a genetic sequence;

(e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected;

(f) an ionic liquid configured as an electrolyte in nanopore sequencer, or a silicone based diffusion pump oil seeded with an ionic liquid;

(g) low pressure viral lysis via the ionic liquid;

a second device located away from the first device, the second device comprising:

(a) an air sampler utilizing aerosol impaction filtration, causing heavier fractions to impact and embed in an end channel, lighter fractions negotiating the change in direction, subsequently lighter fractions can be derived through a stratification based on mass through an airflow;
(b) a cross current or counter current electrospray source employed to nondestructively capture bioaerosols from the air flow, and remove them from the air flow via electrostatic forces;
(c) filtration accomplished using an electrostatic filter, preliminary identification and separation of the virion or biospecies achieved using an ion mobility spectrometer;
(d) bioaerosols accumulated on a witness plate, in preparation for automated sequencing in a sequencer, the sequencer being a nanopore device, and the sequencer outputting a genetic sequence;
(e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected
(f) an ionic liquid configured as an electrolyte in nanopore sequencer, or a silicone based diffusion pump oil seeded with an ionic liquid; and
(g) low pressure viral lysis via the ionic liquid;
a third device located away from the first device and second device, the third device comprising:
(a) an air sampler utilizing aerosol impaction filtration, causing heavier fractions to impact and embed in an end channel, lighter fractions negotiating the change in direction, subsequently lighter fractions can be derived through a stratification based on mass through an airflow;
(b) a cross current or counter current electrospray source employed to nondestructively capture bioaerosols from the air flow, and remove them from the air flow via electrostatic forces;
(c) filtration accomplished using an electrostatic filter, preliminary identification and separation of the virion or biospecies achieved using an ion mobility spectrometer;
(d) bioaerosols accumulated on a witness plate, in preparation for automated sequencing in a sequencer, the sequencer being a nanopore device, and the sequencer outputting a genetic sequence;
(e) electrospray charged pathogens sampled away from an aerosol pre-filter, an image charge produced each time a pathogen particle passes through a flight tube, a viral or bacterial count obtained in addition to m/z charge spectral information about a specific pathogen or virion selected;
(f) an ionic liquid configured as an electrolyte in nanopore sequencer, or a silicone based diffusion pump oil seeded with an ionic liquid; and
(g) low pressure viral lysis via the ionic liquid.

\* \* \* \* \*